(12) United States Patent
Ozawa et al.

(10) Patent No.: US 9,605,107 B2
(45) Date of Patent: Mar. 28, 2017

(54) MODIFIED POLYALKYLENE OXIDE

(71) Applicant: SUMITOMO SEIKA CHEMICALS CO., LTD., Hyogo (JP)

(72) Inventors: Hitoshi Ozawa, Osaka (JP); Tsuyoshi Masuda, Himeji (JP); Yusuke Nishikawa, Himeji (JP)

(73) Assignee: SUMITOMO SEIKA CHEMICALS CO., LTD., Hyogo (JP)

( * ) Notice: Subject to any disclaimer, the term of this patent is extended or adjusted under 35 U.S.C. 154(b) by 147 days.

(21) Appl. No.: 14/408,083

(22) PCT Filed: Jul. 5, 2013

(86) PCT No.: PCT/JP2013/068501
§ 371 (c)(1),
(2) Date: Dec. 15, 2014

(87) PCT Pub. No.: WO2014/007366
PCT Pub. Date: Jan. 9, 2014

(65) Prior Publication Data
US 2015/0183920 A1    Jul. 2, 2015

(30) Foreign Application Priority Data
Jul. 6, 2012   (JP) .................................. 2012-152948

(51) Int. Cl.
| | | |
|---|---|---|
| C08G 63/02 | (2006.01) | |
| C08G 18/48 | (2006.01) | |
| A61K 8/87 | (2006.01) | |
| C08G 18/73 | (2006.01) | |
| C08G 18/75 | (2006.01) | |
| C08G 18/28 | (2006.01) | |
| A61Q 19/00 | (2006.01) | |
| A61K 8/02 | (2006.01) | |
| C08G 18/76 | (2006.01) | |
| C09D 175/04 | (2006.01) | |

(52) U.S. Cl.
CPC ........ *C08G 18/4833* (2013.01); *A61K 8/0216* (2013.01); *A61K 8/87* (2013.01); *A61Q 19/00* (2013.01); *C08G 18/283* (2013.01); *C08G 18/4841* (2013.01); *C08G 18/73* (2013.01); *C08G 18/753* (2013.01); *C08G 18/758* (2013.01); *C08G 18/7621* (2013.01); *C08G 18/7685* (2013.01); *C09D 175/04* (2013.01); *A61K 2800/48* (2013.01)

(58) Field of Classification Search
CPC ..................................................... B32B 27/08
USPC .......... 528/190, 193, 194, 271, 272
See application file for complete search history.

(56) References Cited

U.S. PATENT DOCUMENTS

| | | |
|---|---|---|
| 4,079,028 A | 3/1978 | Emmons |
| 4,155,892 A | 5/1979 | Emmons |
| 5,594,087 A | 1/1997 | Konig |
| 5,612,408 A | 3/1997 | Konig |
| 5,753,731 A | 5/1998 | Yoshioka |

FOREIGN PATENT DOCUMENTS

| | | |
|---|---|---|
| JP | S54-80349 | 6/1979 |
| JP | H07-501094 | 2/1995 |
| JP | H07-76614 | 3/1995 |
| JP | H08-253548 | 10/1996 |
| JP | H09-71766 | 3/1997 |
| JP | 2000-248046 | 9/2000 |
| JP | 2000-303056 | 10/2000 |
| JP | 2002-69430 A1 | 3/2002 |
| JP | 2003-212950 A1 | 7/2003 |
| JP | 2009-1687 A1 | 1/2009 |

(Continued)

OTHER PUBLICATIONS

P. Howard, et al.; "Formulating with Combinations of HEUR Associative Thickeners;" Journal of Coatings Technology; vol. 64; No. 804; Jan. 1992; pp. 87-94 (8 sheets)/p. 3 of specification.

(Continued)

*Primary Examiner* — Terressa Boykin
(74) *Attorney, Agent, or Firm* — Kratz, Quintos & Hanson, LLP (57) ABSTRACT

The object of the present invention is to provide a modified polyalkylene oxide capable of yielding an aqueous solution excellent in transparency with high viscosity, even when combined with a cationic surfactant. The present invention provides a modified polyalkylene oxide obtained by reacting a polyalkylene oxide compound (A), a polyether monohydric alcohol (B), and a diisocyanate compound (C);

wherein W is a polyethylene oxide represented by formula (II)

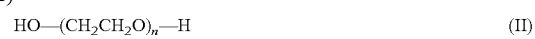

$$HO-(CH_2CH_2O)_n-H \qquad (II)$$

wherein n is an integer of 130 to 680;

wherein (B) comprises a random copolymer of ethylene oxide and propylene oxide, the random copolymer having a hydroxy group at one terminal and a linear-chain $C_{15\text{-}24}$ alkyl group at the other terminal, and having a ratio (a/b) of 1 to 2 wherein a represents the number of moles of ethylene oxide added and b represents the number of moles of propylene oxide added; and wherein (C) is at least one member selected from the group consisting of compounds represented by formula (IV)

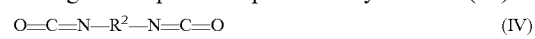

$$O=C=N-R^2-N=C=O \qquad (IV)$$

wherein $R^2$ represents methyldiphenylene, hexamethylene, methyldicyclohexylene, 3-methyl-3,5,5-trimethylcyclohexylene, dimethylphenylene, or tolylene.

9 Claims, 1 Drawing Sheet

(56) References Cited

FOREIGN PATENT DOCUMENTS

| JP | 2009-1688 A1 | 1/2009 |
|----|--------------|--------|
| WO | WO 93/10166 A1 | 5/1993 |
| WO | WO 2008/041347 A1 | 4/2008 |

OTHER PUBLICATIONS

International Search Report for International Application No. PCT/JP2013/068501 dated Jul. 30, 2013.

MODIFIED POLYALKYLENE OXIDE

TECHNICAL FIELD

The present invention relates to a modified polyalkylene oxide.

BACKGROUND ART

Compared with conventional polyacrylic acid-based thickeners, nonionic polyurethane-based thickeners that exhibit thickening properties upon aggregation of hydrophobic groups are recently attracting more attention as thickeners, particularly for products such as cosmetics.

These polyurethane-based thickeners exhibit more increased thickening properties through the association of hydrophobic groups located at the terminals. Because of their nonionic nature, these polyurethane-based thickeners are excellent in salt tolerance, and can suitably be used in combination with ionic surfactants, while being capable of imparting additional rheological properties.

It is known in this field of technology that the thickening properties increase along with an increase in the chain length of hydrophobic groups located at the terminals (Non-Patent Document 1).

Examples of known polyurethane-based thickeners include: those having three hydrophobic groups that are linked through hydrophilic polyester segments of at least 1500 molecular weight each with at least two of the three hydrophobic groups being located at the terminals (Patent Document 1); and those obtained by the reaction of (a) at least one water-soluble polyetherpolyol, (b) at least one water-insoluble organic polyisocyanate, (c) at least one monofunctional hydrophobic organic compound selected from the group consisting of compounds containing a hydrogen atom reactive with an isocyanate and organic monoisocyanates, and (d) at least one polyhydric alcohol or polyhydric alcohol ether (Patent Documents 2 and 3).

Also known are a polyurethane-based thickener characterized by comprising a monohydric alcohol containing at least one other polar group and a trihydric alcohol as a polyhydric alcohol (Patent Document 4) and a viscosity modifier obtained by using a polyether monohydric alcohol containing as a hydrophobic group at least one branched chain or at least one secondary hydrocarbon group (Patent Document 5).

As described in the Non-patent Document, as the number of carbon atoms at the terminal alcohol increases, the thickening properties of the polyurethane-based thickeners obtained by such conventional techniques become greater, due to the increased association power of the hydrophobic groups. However, an increased number of carbon atoms at the terminal alcohol leads to poor affinity for water, and aqueous solutions containing such thickeners are likely to become tacky. For example, when such thickeners are added to cosmetics as a thickening additive, the cosmetics exhibit a heavy feel when used. Another drawback is that because molecular chain terminals modified into hydrophobic groups lower the affinity for water, the aqueous solution becomes turbid. To avoid turbidity, the proportion of hydrophobic groups may be decreased so that the transparency of the aqueous solution is improved. In this case, however, the viscosity decreases when a cationic surfactant (those used particularly for hair care products) is added.

Polyurethane-based thickeners are nonionic. Thus, unlike polyacrylic acid-based thickeners, polyurethane-based thickeners, when used in combination with a cationic surfactant, do not generally produce the precipitation of aggregates resulting from the interaction between cations and anions. However, a polyurethane-based thicker in combination with a cationic surfactant results in a thickened liquid with poor transparency, thereby giving the undesirable appearance.

CITATION LIST

Patent Document

Patent Document 1: JPS54-080349A
Patent Document 2: U.S. Pat. No. 4,155,092
Patent Document 3: U.S. Pat. No. 4,079,020
Patent Document 4: JPH07-501094A
Patent Document 5: JPH09-071766A

Non-Patent Document

Non-patent Document 1: J. Coating Technology Vol. 64, No. 904, pp. 87-94 (1992)

SUMMARY OF INVENTION

Technical Problem

An object of the present invention is to provide a modified polyalkylene oxide capable of yielding an aqueous solution excellent in transparency with high viscosity, even when used in combination with a cationic surfactant.

Solution to Problem

The present inventors conducted extensive research to achieve the above object and found a modified polyalkylene oxide that can be used as a thickener. The modified polyalkylene oxide is configured such that a specific polyalkylene oxide compound is bound at the terminals to specific polyether monohydric alcohols comprising an ethylene oxide/propylene oxide random copolymer and a monohydric alcohol via specific diisocyanates. The inventors also found that such a modified polyalkylene oxide can provide an aqueous solution excellent in transparency, even when combined with a cationic surfactant, and that a small amount of such a modified polyalkylene oxide can achieve high viscosity. The inventors made further improvements and completed the invention.

The present invention includes the subject matter presented in the following items.

Item 1.

A modified polyalkylene oxide obtained by reacting (A) a polyalkylene oxide compound, (B) a polyether monohydric alcohol, and (C) a diisocyanate compound;
wherein the polyalkylene oxide compound (A) is a polyethylene oxide represented by formula (II)

$$\text{HO—(CH}_2\text{CH}_2\text{O)}_n\text{—H} \qquad \text{(II)}$$

wherein n is an integer of 130 to 680;
wherein the polyether monohydric alcohol (B) comprises a random copolymer of ethylene oxide and propylene oxide, the random copolymer having a hydroxy group at one terminal and a linear-chain $C_{15-24}$ alkyl group at the other terminal, and having a ratio (a/b) of 1 to 2 wherein a represents the number of moles of ethylene oxide added and b represents the number of moles of propylene oxide added; and wherein the diisocyanate compound (C) is at least one member selected from the group consisting of compounds represented by formula (IV)

$$O=C=N-R^2-N=NC=O \quad \text{(IV)}$$

wherein $R^2$ represents methyldiphenylene, hexamethylene, methyldicyclohexylene, 3-methyl-3,5,5-trimethylcyclohexylene, dimethylphenylene, or tolylene, Item 2.

The modified polyalkylene oxide according to Item 1, wherein the polyalkylene oxide compound (A) has a number average molecular weight of 6,000 to 30,000.

Item 3.

The modified polyalkylene oxide according to Item 1 or 2, wherein, with respect to the polyether monohydric alcohol (B), a is an integer of 5 to 10, and h is an integer of 5 to 8.

Item 4.

The modified polyalkylene oxide according to any one of Items 1 to 3, wherein the polyether monohydric alcohol (B) has a number average molecular weight of 800 to 3,000.

Item 5.

The modified polyalkylene oxide according to any one of Items 1 to 4, wherein the diisocyanate compound (C) is at least one member selected from the group consisting of dicyclohexylmethane-4,4'-diisocyanate, and 1,6-hexamethylene diisocyanate.

Item 6.

The modified polyalkylene oxide according to any one of Items 1 to 5, wherein the reaction is carried out using 1 to 2 moles of the polyether monohydric alcohol (B) per mole of the polyalkylene oxide compound (A).

Item 7.

A cosmetic composition comprising the modified polyalkylene oxide according to any one of Items 1 to 6 (preferably in an amount of 0.01 to 5% by mass).

Item 8.

The cosmetic composition according to Item 7, further comprising a cationic surfactant (preferably in an amount of 0.1 to 2% by mass).

Item 9.

A molded article prepared by using the modified polyalkylene oxide according to any one of Items 1 to 6.

Item 10.

The molded article according to Item 9, which is in the form of a sheet or a film.

Advantageous Effects of Invention

The modified polyalkylene oxide according to the present invention, even in combination with a cationic surfactant, maintains the excellent transparency of a solution without decreasing viscosity. Thus, the use of the modified polyalkylene oxide according to the present invention can provide a transparent and highly viscous aqueous solution.

DESCRIPTION OF EMBODIMENTS

The modified polyalkylene oxide according to the present invention is obtained by reacting a specific polyalkylene oxide compound (A), a specific polyether monohydric alcohol (B), and a specific diisocyanate compound (C). Hereinafter, these components may be simply referred to as (A), (B), and (C).

(A) is a polyethylene oxide represented by formula (II):

$$HO-(CH_2CH_2O)_n-H \quad \text{(II)}$$

wherein n is an integer of 130 to 680.

The polyethylene oxide preferably has a number average molecular weight of about 6,000 to 30,000, and more preferably about 11,000 to 20,000.

The use of (A) having a number average molecular weight of 6,000 or more is less likely to cause a decrease in transparency of an aqueous solution of the modified polyalkylene oxide. The use of (A) having a number average molecular weight of 30,000 or less is less likely to cause a decrease in viscosity of an aqueous solution of the modified polyalkylene oxide.

The number average molecular weight of the polyethylene oxide (A) is determined from the following formula using the hydroxyl number $O_1$ determined in accordance with method A in JIB K 1557-1:2007 (Plastics—Polyols for Use in the Production of Polyurethane—Part 1: Determination of Hydroxyl Number). Specifically, the number average molecular weight is determined from the following formula assuming that the polyethylene oxide has a hydroxyl group at each end.

Number average molecular weight=$(56,100 \times 2)/O_1$ (B) is a polyether monohydric alcohol having a structure in which a random copolymer of ethylene oxide (EO) and propylene oxide (PO) has a hydroxy group at one terminal and a linear-chain alkyl group at the other terminal (hereinafter, the alkyl group will sometimes be referred to as $R^1$). When a represents the number of moles of ethylene oxide added, and b represents the number of moles of propylene oxide added, the a/b ratio is in the range of 1 to 2.

The polyether monohydric alcohol may also be termed "polyoxyethylene polyoxypropylene monoalkyl ether in which ethylene oxide is randomly copolymerized with propylene oxide in the molar ratio (a/b) of 1 to 2 (preferably 1.1 to 1.5) and a $C_{15-24}$ linear-chain alkyl group is present."

(B) may be represented by the following formula (III):

$$R^1-[(OCH_2CH_2)_a\text{-ran-}(OCH_2CH(CH_3))_b]-OH \quad \text{(III)}$$

wherein, $R^1$ represents a linear-chain $C_{15-24}$ alkyl group.

The part $[(OCH_2CH_2)_a\text{-ran-}(OCH_2CH(CH_3))_b]$ indicates that the constitutional units $(OCH_2CH_2)$ and $(OCH_2CH(CH_3))$ are randomly copolymerized. The degree of polymerization of each constitutional unit is represented by a and b. From this, it is clear that the [ran] in $[\alpha_i\text{-ran-}\beta_j]$ indicates that the constitutional units α and β are randomly copolymerized at the polymerization degree of i and j, respectively.

The a/b ratio of (B) is 1 to 2 as stated above, and preferably 1.1 to 1.5. The ratio of less than 1 is not preferable because the obtained modified polyalkylene oxide becomes less water soluble, and thus the aqueous solution exhibits decreased transparency. The ratio of more than 2 is not preferable because the aqueous solution becomes less viscous, and exhibits decreased transparency, particularly when the obtained modified polyalkylene oxide is used in combination with a cationic surfactant.

Preferably, a is an integer of 5 to 10. Preferably, b is an integer of 5 to 8. More preferably, a is an integer of 5 to 10 whereas h is an integer of 5 to 8. When a is 5 or more, an aqueous solution of the obtained modified polyalkylene oxide can exhibit increased viscosity. When a is 10 or less, an aqueous solution of the obtained modified polyalkylene oxide can exhibit increased transparency. When b is 5 or more, an aqueous solution of the obtained modified polyalkylene oxide can exhibit increased transparency. When b is 8 or less, an aqueous solution of the obtained modified polyalkylene oxide can exhibit increased viscosity.

As stated above, $R^1$ is a linear-chain $C_{15-24}$ alkyl, preferably a linear-chain $C_{16-22}$ and more preferably a linear-chain alkyl. When the number of carbon atoms is 15 or more, an aqueous solution of the obtained modified polyalkylene oxide can exhibit increased viscosity. When the number of carbon atoms is 24 or less, an aqueous solution of the obtained modified polyalkylene oxide can exhibit increased transparency.

(B) is configured such that a random copolymer of propylene oxide and ethylene oxide (polyalkylene oxide) is added to a linear-chain monohydric saturated alcohol.

If the random copolymer of propylene oxide and ethylene oxide is, for example, a blocked copolymer of propylene oxide and ethylene oxide, the obtained modified polyalkylene oxide becomes less water soluble, and thus, the aqueous solution exhibits decreased transparency. Therefore, a blocked copolymer of propylene oxide and ethylene oxide is not preferable.

(B) can be prepared, for example, by addition polymerization of ethylene oxide and propylene oxide to a linear-chain monohydric saturated alcohol. The linear-chain monohydric saturated alcohol is a linear-chain saturated alcohol having 15 to 24 (preferably 16 to 22, and more preferably 16 to 20) carbon atoms.

For the addition polymerization of ethylene oxide and propylene oxide to a linear-chain monohydric saturated alcohol, ordinary methods may be employed. For example, the addition polymerization may be carried out by using radical polymerization employing a peroxide or an azo group-containing polymerization initiator or by using a thiol group-containing polymerization-chain-transfer agent that readily causes a chain-transfer reaction.

(B) preferably has a number average molecular weight of 800 to 3,000, and more preferably 1,000 to 2,500. When the number average molecular weight is 800 or more, an aqueous solution of the obtained modified polyalkylene oxide can exhibit increased viscosity. When the number average molecular weight is 3,000 or less, an aqueous solution of the obtained modified polyalkylene oxide is less likely to exhibit decreased viscosity even in the presence of cations.

The number average molecular weight of (B) can be determined from the following formula using the hydroxy number $O_1$ determined in accordance with method A in JIS K 1557-1:2007 (Plastics—Polyols for Use in the Production of Polyurethane—Part 1: Determination of Hydroxyl Number). Specifically, the number average molecular weight is determined from the following formula assuming that the polyethylene oxide has a hydroxy group at one end.

Number Average Molecular Weight=(56,100)/$O_1$ (B) is preferably contained in an amount of a to 2 moles, more preferably 1.1 to 2 moles, and still more preferably 1.5 to 2 moles, per mole of (A) When (B) is contained in an amount of 1 mole or more per mole of (A), an aqueous solution of the obtained modified polyalkylene oxide is less likely to exhibit decreased viscosity. When a polyether monohydric alcohol is contained in an amount of 2 moles or less per mole of (A), an aqueous solution of the obtained modified polyalkylene oxide can exhibit increased transparency.

(C) is a diisocyanate compound represented by formula (IV):

wherein $R^2$ represents methyldiphenylene, hexamethylene, methyldicyclohexylene, 3-methyl-3,5,5-trimethylcyclohexylene, dimethylphenylene, or tolylene.

Specific examples of (C) include 4,4'-diphenylmethane diisocyanate (MDI), 1,6-hexamethylene diisocyanate (HDI), dicyclohexylmethane-4,4'-diisocyanate (HMDI), 3-isocyanatemethyl-3,5,5-trimethyl cyclohexylisocyanate (IPDI), 1,8-dimethylbenzole-2,4-diisocyanate, and 2,4-tolylene diisocyanate (TDI). Among these diisocyanate compounds, dicyclohexylmethane-4,4'-diisocyanate (HMDI), and 1,6-hexamethylene diisocyanate (HDI) are preferable from the standpoint of excellent weatherability and transparency imparted to the obtained modified polyalkylene oxide. These diisocyanate compounds may be used singly or in a combination of two or more.

With respect to the amount of the diisocyanate compound for use, when the total amount of the terminal hydroxy groups in (A) and (B) (molar amount of [—OH]) is taken as a mole, the molar amount of isocyanate groups in the isocyanate compound (molar amount of [—NCO]) is preferably 0.8 to 1.2, and more preferably 0.9 to 1.1. In other words, the isocyanate groups are preferably present in an amount of 0.8 to 1.2 moles, and more preferably 0.9 to 1.1 moles, in the isocyanate compound when the total amount of the terminal hydroxy groups in (A) and (B) is taken as a mole. When the isocyanate group is present in an amount of 0.8 mole or more, not much unreacted polyether monohydric alcohol remains, and an aqueous solution of the obtained modified polyalkylene oxide is less likely to exhibit decreased viscosity. When the isocyanate group is present in an amount of 1.2 moles or less, the water solubility can be improved.

The modified polyalkylene oxide according to the present invention can be obtained by reacting (A), (B), and (C), as stated above, and the compound represented by the following formula (I) is considered to be the major component.

[Chem. 1]

In the formula (I), $R^1$, $R^2$, a, b, [(OCH$_2$CH$_2$)$_a$-ran-(OCH$_2$CH(CH$_3$))$_b$], and n are as defined above, and m is an integer of 1 to 4.

Examples of methods for reacting a polyalkylene oxide compound (A), a polyether monohydric alcohol (B), and a diisocyanate compound (C) include: methods comprising the step of dissolving or dispersing (A), (B), and (C) in a reaction solvent, such as toluene, xylene, and dimethylformamide, to carry out a reaction; and methods comprising the steps of pulverizing solids into powders (powders) or melting solids into liquids, uniformly mixing them, and heating the mixture to a predetermined temperature for reaction. From the standpoint of industrial practice, a preferable method comprises the steps of continuously supplying heated and melted starting materials to a multi-screw extruder and mixing them in the extruder for reaction. The reaction temperature is preferably 70 to 210° C., more preferably 90 to 180° C., and still more preferably 100 to 160° C. The reaction time is suitably determined such that the reaction is complete, depending on the reaction temperature and the type of the polyalkylene oxide compound, polyether monohydric alcohol, and diisocyanate compound to be used. As used herein, the reaction time refers to the mean residence time in the multi-screw extruder, which is determined by the following procedure. A trace of colorant (e.g., pulverized red chalk or blue No. 5) is supplied to a multi-screw extruder simultaneously with a polyalkylene oxide compound, a polyether monohydric alcohol, and a diisocyanate compound, and the change in color of the discharged substance is observed. The time at which a portion with the deepest color is discharged is determined as the mean residence time. To achieve a mean resident time of 0.5 to 5.0 minutes, preferably 1.0 to 3.5 minutes, and more preferably 1.5 to 3.0 minutes, the amount of supply, the rotation speed, and the shape of the screws can be adjusted.

In the preparation of a modified polyalkylene oxide, a small amount of a reaction accelerator, such as triethylamine, triethanolamine, dibutyltin diacetate, dibutyltin dilaurate, stannous octoate, and triethylenediamine, can be added to the reaction system to promote the reaction. The amount of the reaction accelerator to be added is preferably 200 to 2,000 mass ppm, and more preferably 500 to 1,000 mass ppm, based on the polyalkylene oxide compound.

As described above, a modified polyalkylene oxide can be obtained by mixing a polyalkylene oxide compound, a polyether monohydric alcohol, and a diisocyanate compound in a suitable reactor, such as an extruder, and subjecting the mixture to a reaction. A modified polyalkylene oxide is obtained as a mixture largely comprising a component in which a polyalkylene oxide compound and a diisocyanate compound are repeatedly polymerized such that m in formula (I) is about 1 to 4. The mixture can be used without separation. The mixing ratio can be examined by a separation technique such as GPC. In particular, a component polymerized such that m is 1 to 2 is the main product.

In particular, the obtained modified polyalkylene oxide can be used preferably in the production of cosmetics. The obtained modified polyalkylene oxide can be added and dissolved during the production process of cosmetics. The obtained modified polyalkylene oxide can preferably be added in an amount of 0.01 to 5% by mass, and more preferably 0.05 to 3% by mass. In other words, the present invention encompasses a cosmetic composition containing the modified polyalkylene oxide; in particular, a cosmetic composition containing the modified polyalkylene oxide in the aforementioned amount is preferable. The obtained modified polyalkylene oxide, when contained in an amount of 0.01% by mass or more, produces the thickening effect more preferably. When the obtained modified polyalkylene oxide is contained in an amount of 5% by mass or less, the likelihood of gelling is more decreased. The obtained, modified polyalkylene oxide can also be used after being diluted, for example, with water; an aqueous solution containing a salt, such as sodium chloride, or a surfactant; an aqueous solution of diethylene glycol monobutyl ether, triethylene glycol monobutyl ether, polypropylene glycol, propylene glycol, or the like; and polyethylene glycol 200. For example, the obtained modified polyalkylene oxide can be diluted to a concentration of 5 to 50% by mass before use. To shorten the dissolution time period, the obtained modified polyalkylene oxide can be milled before use. For example, the obtained modified polyalkylene oxide is milled to a median particle size of about 100 μm. Although the milling technique is not limited, cryomilling in liquid nitrogen is optimally used. As used herein, the median particle size refers to the median size determined by a dry sieving method (JIS Z8815). Specifically, 50 g of a resin (modified polyalkylene oxide) is weighed out, and sieved by using JIS standard sieves (JIS Z8801), followed by weighing the resin of each sieve. The results indicate the point at which the cumulative percentage by mass of the resin retained in each sieve is 50%, and the particle size at that point is considered to be the median particle size.

Because of its nonionic nature, the modified polyalkylene oxide according to the present invention causes little change in viscosity when used in combination with a nonionic, anionic, or cationic surfactant, or a salt. In particular, the modified polyalkylene oxide can be used in an excellent manner in combination with cationic surfactants, which has conventionally been difficult to do. Even when the modified polyalkylene oxide is used in combination with a cationic surfactant, high transparency is retained. Examples of cationic surfactants, although not being particularly limited, include alkyl trimethyl ammonium chloride, stearyl trimethyl ammonium chloride, stearyl trimethyl ammonium bromide, cetostearyl trimethyl ammonium chloride, distearyl dimethyl ammonium chloride, stearyl dimethyl benzyl ammonium chloride, behenyl trimethyl ammonium bromide, benzalkonium chloride, behenic acid amide propyldimethyl hydroxypropyl ammonium chloride, stearic acid diethylaminoethyl amide, stearic acid dimethylaminopropylamide, and lanolin-derived quaternary ammonium salts.

Although there is no particular limitation, the modified polyalkylene oxide according to the present invention preferably has a number average molecular weight of 10,000 or more, more preferably 10,000 to 50,000, still more preferably 12,000 to 45,000, and still further preferably 15,000 to 40,000. The number average molecular weight in this specification is determined by GPC analysis under the conditions described in "GPC Analysis" in the Examples below.

The present invention preferably encompasses a composition that contains, in addition to the modified polyalkylene oxide according to the present invention, a surfactant or a salt as described above (particularly a cationic surfactant). Such a composition contains a surfactant or a salt in an amount of, for example, 1.0 to 2% by mass, and preferably 0.2 to 1.5% by mass. In particular, the composition is preferably a cosmetic composition, and more preferably a hair care composition. A common technique can be employed for producing such a cosmetic composition or hair care composition, and the composition may contain other components. Other components are not particularly limited, and those commonly used for cosmetics, such as moisturizers (e.g., glycol), antibacterial components (e.g., polylysine), colorants, fragrances, antioxidants, UV absorbers, and plant extracts, can be added.

The viscosity of a 2% by mass aqueous solution of the modified polyalkylene oxide according to the present invention can be determined by measuring the viscosity at a shear rate of 0.001 to 1,000 [l/s] at 25° C. using a cone-and-plate rheometer (AR2000 manufactured by TA Instruments) with a cone (60 mm, cone angle: 1°). Although there is no particular limitation, a 2% by mass aqueous solution of the modified polyalkylene oxide according to the present invention preferably has a viscosity of about 100 to 300 [Pa·s] at a shear rate of 1 [l/s] as measured above. A cone-and-plate rheometer can detect viscous behavior in more detail than conventional B-type viscometers.

The transparency of the modified polyalkylene oxide according to the present invention can be evaluated on the basis of light transmission at 425 nm that is measured by using a UV-visible spectrophotometer after placing a 1% by mass aqueous solution of the modified polyalkylene oxide on a quartz glass having an optical path length of 1 cm. The light transmittance determined in the above manner is preferably 70% or more, more preferably 80% or more, and still more preferably 90% or more. A cosmetic product that contains such a modified polyalkylene oxide having a light transmittance of 70% or more exhibits more increased transparency. Although conventional polyacrylic acid-based thickeners can provide an aqueous solution having a light transmittance of 90% or higher, such thickeners are not preferable because the aqueous solution becomes inhomogeneous and less viscous due to the precipitation of the polymer when the thickeners are used in combination with a cationic surfactant, which is useful for hair care products.

The modified polyalkylene oxide according to the present invention can be processed into various molded articles using a device, such as a kneader, a roll, an extruder, and a hot press. In particular, the modified polyalkylene oxide is suitably processed into flexible molded articles, such as sheets and films. A fragrance and/or a surfactant can also be added in the molding process. The molded articles produced from the modified polyalkylene oxide according to the present invention are easily dissolved in water. In particular, the sheets and films produced from the modified polyalkylene oxide according to the present invention are water soluble, and can be easily dissolved in a small amount of moisture. Such sheets and films can suitably be used for cosmetic materials, such as facial masks, because of their quick dissolution in water, skin toner, and milky lotion for the skin, as well as their excellent adhesion. Additionally, such sheets and films can suitably be used, for example, for toiletry cleaning products due to their speedy dissolution in sewage.

The modified polyalkylene oxide according to the present invention can also be molded by melt-mixing with another thermoplastic resin when molded, and can thus be used to improve the hydrophilicity and smoothness of the surface of the resin.

EXAMPLES

Hereinafter, Production Examples, Examples, and Comparative Examples describe the present invention in more detail. However, the present invention is not limited to the Production Examples and Examples.
Evaluation Method
(1) Viscosity of Aqueous Solution 6.0 g of a modified polyalkylene oxide was individually added to 294 g of ion-exchanged water and 294 g of an aqueous solution containing 1% by mass of stearyl trimethyl ammonium chloride, which is a cationic surfactant. The mixtures were stirred at 30° C. at 300 rpm for 3 hours, thereby giving aqueous solutions containing 2% by mass of a modified polyalkylene oxide.

The viscosity of the obtained aqueous solutions was measured at a shear rate in the range of 0.001 to 1,000 [l/s] at 25° C. using a cone-and-plate rheometer (AR2000 manufactured by TA Instruments Inc.) with a cone (60 mm, cone angle 1°).
(2) Transparency An aqueous solution containing 2% by mass of a modified polyalkylene oxide and an aqueous solution containing 2% by mass of a modified polyalkylene oxide and 1.0% by mass of stearyl trimethyl ammonium chloride were prepared in the same manner as in the above section (1). 4.5 mL of each of the solutions was centrifuged (1,800 rpm) to remove bubbles, and measured for light transmittance at 425 urn with a UV-visible spectrophotometer (UV-3150: Shimadzu Corp.) to evaluate transparency.
(3) GPC Analysis 0.5 g of a modified polyalkylene oxide was dissolved in 49.5 g of DMF while heating, and the molecular weight (PEO conversion) and the distribution thereof were determined by the following GPC. PEO is the abbreviation for polyethylene oxide, and the PEO conversion indicates the molecular weight of a modified polyalkylene oxide determined from a calibration curve created by using a PEO of a known molecular weight as a molecular weight marker of GPC.
Carrier: DMF (LiBr 0.1 mmol/L)
Column: Tosoh TSKgel MultiporeHXL-M×3
(Exclusion limit 2,000,000: Polystyrene)
Pump Flow Rate: 0.6 mL/min
(4) Median Particle Size Measurement The median particle size was determined by a dry sieving method (JIS Z8815). Specifically, 50 g of a resin was weighed out, and sieved by using JIS standard sieves (JIS Z8801). The resin of each sieve was weighed, and the particle size at the point, of cumulative mass of 50% was determined on the basis of the results.

Example 1

100 parts by mass of a fully dehydrated polyethylene oxide having a number average molecular weight of 20,000, 7.4 parts by mass of polyether stearyl alcohol $CH_3(CH_2)_{17}O—[(CH_2CH_2O)_8\text{-ran-}(CH_2CH(CH_3)O)_6]—H$ (Blaunon SA50/50 manufactured by Aoki Oil industrial Co., Ltd, number average molecular weight: 1,000), and 0.2 parts by mass of dioctyltin dilaurate were placed in a stirrer-equipped storage tank A heated to 80° C. The mixture was stirred in a nitrogen gas atmosphere, thereby giving a homogeneous mixture.

Apart from this, dicyclonexylmethane-4,4'-diisocyanate was placed in a storage tank B heated to 30° C., and stored in a nitrogen gas atmosphere.

The mixture in the storage tank A and the dicyclohexylmethane-4,4'-diisocyanate in the storage tank B were continuously supplied at a rate of 200 [g/min] and 4.24 [g/min], respectively, by using a metering pump to a biaxial extruder having screws with a 26-mm outer diameter (L/D=40), which was set at 110 to 140° C., to mix them and carry out a reaction in the extruder. Strands were extruded from the outlet of the extruder and pelletized by using a pelletizer, thereby giving a modified polyalkylene oxide.

GPC analysis revealed that the obtained modified polyalkylene oxide was a mixture of components, and the distribution of each component was described by referring to formula (I) as follows: m=1 was 55%, m=2 was 25%, m=3 was 15%, and m=4 was 5%. GPC analysis also revealed that the number average molecular weight was 36,700. After being immersed in liquid nitrogen, the obtained pellets were milled to a median particle size of 100 μm, and used for evaluation.

Tables 1 and 2, respectively, show the starting materials used and evaluation results.

Example 2

100 parts by mass of a fully dehydrated polyethylene oxide having a number average molecular weight of 11,000, 14.0 parts by mass of polyether stearyl alcohol $CH_3(CH_2)_{17}O—[(CH_2CH_2O)_8\text{-ran-}(CH_2CH(CH_3)O)_6]—H$ (Blaunon SA50/50 manufactured by Aoki Oil Industrial Co., Ltd, number average molecular weight: 1,000), and 0.2 parts by mass of dioctyltin dilaurate were placed in a stirrer-equipped storage tank A heated to 80° C., and stirred in a nitrogen gas atmosphere, thereby giving a homogeneous mixture.

Apart from this, 1,6-hexamethylene diisocyanate was placed in a storage tank B heated to 30° C., and stored in a nitrogen gas atmosphere.

The mixture in the storage tank A and the 1,6-hexamethylene diisocyanate in the storage tank B were continuously supplied at a rate of 250 [g/min] and 5.93 [g/min], respectively, by using a metering pump to a biaxial extruder having screws with a 26-mm outer diameter (L/D=40), which was set at 110 to 140° C., to mix them and carry out a reaction in the extruder. Strands were extruded from the outlet of the extruder and pelletized by a pelletizer, thereby giving a modified polyalkylene oxide. GPC analysis revealed that the obtained modified polyalkylene oxide was a mixture of components, and the distribution of each component was described by referring to formula (I) as follows: m=1 was 60%, m=2 was 25%, m=3 was 10%, and m=4 was 5%. GPC analysis also revealed that the number average molecular weight was 20,000. After being immersed in liquid nitrogen, the obtained pellets were milled to a median particle size of 100 μm, and used for evaluation.

Tables 1 and 2, respectively, show the starting materials used and evaluation results.

Example 3

100 parts by mass of a fully dehydrated polyethylene oxide having a number average molecular weight of 20,000, 8.3 parts by mass of polyether cetyl alcohol $CH_3(CH_2)_{15}O—[(CH_2CH_2O)_{10}\text{-ran-}(CH_2CH(CH_3)O)_8]—H$ (Unisafe 10P-8 manufactured by NOF Corporation, number average molecular weight: 1,150), and 0.2 parts by mass of dioctyltin dilaurate were placed in a stirrer-equipped storage tank A heated to 80° C., and stirred in a nitrogen gas atmosphere, thereby giving a homogeneous mixture.

Apart from this, dicyclohexylmethane-4,4'-diisocyanate was placed in a storage tank B heated to 30° C., and stored in a nitrogen gas atmosphere.

The mixture in the storage tank A and the dicyclohexylmethane-4,4'-diisocyanate in the storage tank B were continuously supplied at a rate of 220 [g/min] and 4.59 [g/min], respectively, by using a metering pump to a biaxial extruder having screws with a 26-mm outer diameter (L/D=40), which was set at 110 to 140° C. to mix them and carry out a reaction in the extruder. Strands were extruded from the outlet of the extruder and pelletized by a pelletizer, thereby giving a modified polyalkylene oxide. GPC analysis revealed that the obtained modified polyalkylene oxide was a mixture of components, and the distribution of each component was described by referring to formula (I) as follows: m=1 was 55%, m=2 was 20%, m=3 was 15%, and m=4 was 10%. GPC analysis also revealed that the number average molecular weight was 39,000. After being immersed in liquid nitrogen, the obtained pellets were milled to a median particle size of 100 μm, and used for evaluation.

Tables 1 and 2, respectively, show the starting materials used and evaluation results.

Comparative Example 1

100 parts by mass of a fully dehydrated polyethylene oxide having a number average molecular weight of 20,000, 6.7 parts by mass of polyether stearyl alcohol $CH_3(CH_2)_{17}O—[(CH_2CH_2O)_4\text{-ran-}(CH_2CH(CH_3)O)_7]—H$ (Blaunon SA30/70 manufactured by Aoki Oil Industrial Co., Ltd, number average molecular weight: 900), and 0.2 parts by mass of dioctyltin dilaurate were placed in a stirrer-equipped storage tank A heated to 80° C., and stirred in a nitrogen gas atmosphere, thereby giving a homogeneous mixture.

Apart from this, dicyclohexylmethane-4,4'-diisocyanate was placed in a storage tank B heated to 30° C., and stored in a nitrogen gas atmosphere.

The mixture in the storage tank A and the dicyclohexylmethane-4,4'-diisocyanate in the storage tank B were continuously supplied at a rate of 200 [g/min] and 4.29 [g/min], respectively, by using a metering pump to a biaxial extruder having screws with a 26-mm outer diameter (L/D=40), which was set at 110 to 140° C., to mix them and carry out a reaction in the extruder. Strands were extruded from the outlet of the extruder and pelletized by a pelletizer, thereby giving a modified polyalkylene oxide. GPC analysis revealed that the obtained modified polyalkylene oxide was a mixture of components, and the distribution of each component was described by referring to formula (I) as follows: m=1 was 55%, m=2 was 30%, m=3 was 10%, and m=4 was 5%. GPC analysis also revealed that the number average molecular weight was 35,500. After being immersed in liquid nitrogen, the obtained pellets were milled to a median particle size of 100 μm, and used for evaluation.

Tables 1 and 2, respectively, show the starting materials used and evaluation results.

Comparative Example 2

100 parts by mass of a fully dehydrated polyethylene oxide having a number average molecular weight of 11,000, 13.6 parts by mass of polyether behenyl alcohol $CH_3(CH_2)_{21}O—[(CH_2CH_2O)_{15}\text{-ran-}(CH_2CH(CH_3)O)_1]—H$ (Penal BEP-0115 manufactured by Toho Chemical Industry Co., Ltd, number average molecular weight: 1,040), and 0.2 parts by mass of dioctyltin dilaurate were placed in a stirrer-equipped storage tank A heated to 80° C., and stirred in a nitrogen gas atmosphere, thereby giving a homogeneous mixture.

Apart from this, 1,6-hexamethylene diisocyanate was placed in a storage tank B heated to 30° C., and stored in a nitrogen gas atmosphere.

The mixture in the storage tank A and the 1,6-hexamethylene diisocyanate in the storage tank B were continuously supplied at a rate of 250 [g/min] and 5.78 [g/min], respectively, by using a metering pump to a biaxial extruder having screws with a 26-mm outer diameter (L/D=40), which was set at 110 to 140° C., to mix them and carry out a reaction in the extruder. Strands were extruded from the outlet of the extruder and pelletized by a pelletizer, thereby giving a modified polyalkylene oxide. GPC analysis revealed that the obtained modified polyalkylene oxide was a mixture of components, and the distribution of each component was described by referring to formula (I) as follows: m=1 was 50%, m=2 was 35%, m=3 was 10%, and m=4 was 5%. GPC analysis also revealed that the number average molecular weight was 21,200. After being immersed in liquid nitrogen, the obtained pellets were milled to a median particle size of 100 μm, and used for evaluation.

Tables 1 and 2, respectively, show the starting materials used and evaluation results.

Comparative Example 3

100 parts by mass of a fully dehydrated polyethylene oxide having a number average molecular weight of 20,000, 3.2 parts by mass of polyether stearyl ether $C_{18}H_{37}O$—$(CH_2CH_2O)_{20}$—H (Nonion S-220 manufactured by NOF Corporation, molecular weight: 1,150), and 0.2 parts by mass of dioctyltin dilaurate were placed in a stirrer-equipped storage tank A heated to 80° C., and stirred in a nitrogen gas atmosphere, thereby giving a homogeneous mixture.

Apart from this, dicyclohexylmethane-4,4'-diisocyanate was placed in a storage tank B heated to 30° C., and stored in a nitrogen gas atmosphere.

The mixture in the storage tank A and the dicyclohexylmethane-4,4'-diisocyanate in the storage tank B were continuously supplied at a rate of 250 [g/min] and 2.43 [g/min], respectively, by using a metering pump to a biaxial extruder having screws with a 26-mm outer diameter (L/D=40), which was set at 110 to 140° C., to mix them and carry out a reaction in the extruder. Strands were extruded from the outlet of the extruder and pelletized by a pelletizer, thereby giving a modified polyalkylene oxide. GPC analysis revealed that the obtained modified polyalkylene oxide was a mixture of components, and the distribution of each component was described by referring to formula (I) as follows: m=1 was 55%, m=2 was 15%, m=3 was 25%, and m=4 was 5%. GPC analysis also revealed that the number average molecular weight was 31,100. After being immersed in liquid nitrogen, the obtained pellets were milled to a median particle size of 100 μm, and used for evaluation.

Tables 1 and 2, respectively, show the starting materials used and evaluation results.

Comparative Example 4

100 parts by mass of a fully dehydrated polyethylene oxide having a number average molecular weight of 4,000, 36.0 parts by mass of polyether stearyl alcohol $CH_3(CH_2)_{17}O$—$[(CH_2CH_2O)_8$-ran-$(CH_2CH(CH_3)O)_6]$—H (Blaunon SA50/50 manufactured by Aoki Oil Industrial. Co., Ltd, number average molecular weight: 1,000), and 0.2 parts by mass of dioctyltin dilaurate were placed in a stirrer-equipped storage tank A heated to 80° C., and stirred in a nitrogen gas atmosphere, thereby giving a homogeneous mixture.

Apart from this, dicyclohexylmethane-4,4'-diisocyanate was placed in a storage tank B heated to 30° C., and stored in a nitrogen gas atmosphere.

The mixture in the storage tank A and the dicyclohexylmethane-4,4'-diisocyanate in the storage tank B were continuously supplied at a rate of 200 [g/min] and 16.57 [g/min], respectively, by using a metering pump to a biaxial extruder having screws with a 26-mm outer diameter (L/D=40), which was set at 110 to 140° C., to mix them and carry out a reaction in the extruder. Strands were extruded from the outlet of the extruder and pelletized by a pelletizer, thereby giving a modified polyalkylene oxide. GPC analysis revealed that the obtained modified polyalkylene oxide was a mixture of components, and the distribution of each component was described by referring to formula (I) as follows: m=1 was 50%, m=2 was 35%, m=3 was 10%, and m=4 was 5%. GPC analysis also revealed that the number average molecular weight was 9,500. After being immersed in liquid nitrogen, the obtained pellets were milled to a median particle size of 100 μm, and used for evaluation.

Tables 1 and 2, respectively, show the starting materials used and evaluation results.

Figure 1:
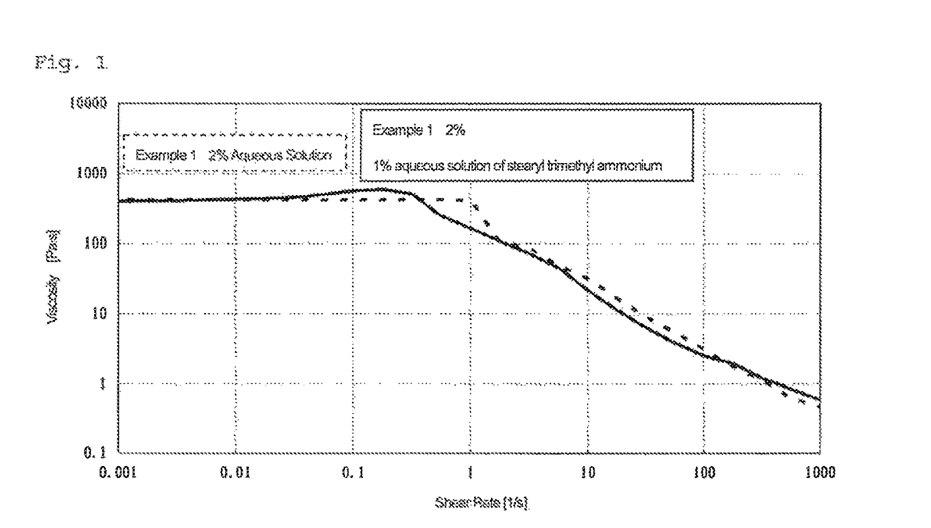
FIG. 1 shows the correlation between the shear rate and the viscosity of an aqueous solution of the modified polyalkylene oxide prepared in Example 1 (2% by mass aqueous solution).
Figure 2:
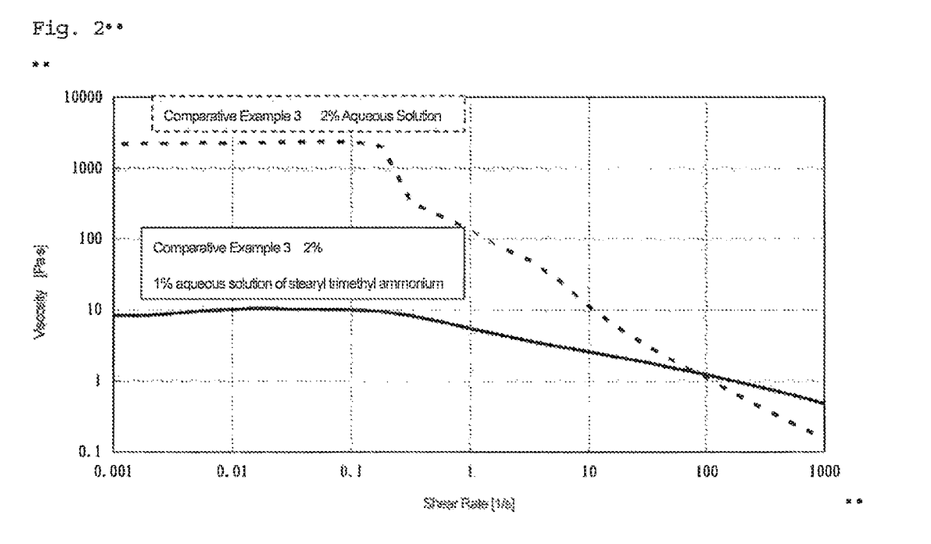
FIG. 2 shows the correlation between the shear rate and the viscosity of an aqueous solution of the modified polyalkylene oxide prepared in Comparative Example 3 (2% by mass aqueous solution).

FIGS. 1 and 2 show the results of viscosity measurement of Example 1 and Comparative Example 3.

In Table 1, Mn indicates a number average molecular weight. In Table 1, n, m, a, b, and $R^1$ are defined as in formulae (I) to (IV) above.

Example 4

The modified polyalkylene oxide obtained in Example 1 was molded into a sheet of 10 cm×10 cm×0.01 cm by using a hot press (manufactured by Gonno Suiatzuki Seisakusho, 40 t press, pressure: 4.9 MPa·G) set at 160° C.

The obtained sheet, when folded in half along the center line at 180 degrees, exhibited sufficient flexibility and strength without being fractured. Further, after the obtained sheet was cut into a 5 cm×5 cm piece and immersed in 200 mL of on-exchanged water at 25° C. in a 300 mL beaker, the cut-out piece was fully dissolved in 10 seconds.

TABLE 1

| | Polyalkylene Oxide [1] (A) | | | Polyether Monohydric Alcohol (B) | | | | | | Modified Polyalkylene Oxide Mixture | | | | | |
|---|---|---|---|---|---|---|---|---|---|---|---|---|---|---|---|
| | | | | EO | PO | EO/PO | | | | | Proportion [%] | | | | |
| | Species | n | Molecular Weight | Molar Number (a) | Molar Number (b) | Molar Ratio a/b | R1 C Number | Molar Ratio B/A | Diisocyanate [2] (C) | NCO/ OH | m = 1 | m = 2 | m = 3 | m = 4 | Mn |
| Example 1 | Poly-EO | 450 | 20000 | 8 | 6 | 1.3 | 18 | 1.48 | HMDI | 1.00 | 55 | 25 | 15 | 5 | 36,700 |
| Example 2 | Poly-EO | 250 | 11000 | 8 | 6 | 1.3 | 18 | 1.64 | HDI | 1.00 | 60 | 25 | 10 | 5 | 20,000 |
| Example 3 | Poly-EO | 450 | 20000 | 10 | 8 | 1.3 | 16 | 1.46 | HMDI | 1.00 | 55 | 20 | 15 | 10 | 39,000 |
| Comp. Example 1 | Poly-EO | 450 | 20000 | 4 | 7 | 0.6 | 18 | 1.49 | HMDI | 1.00 | 55 | 30 | 10 | 5 | 35,500 |
| Comp. Example 2 | Poly-EO | 250 | 11000 | 15 | 1 | 15.0 | 22 | 1.44 | HDI | 1.00 | 50 | 35 | 10 | 5 | 21,200 |

TABLE 1-continued

| | Polyalkylene Oxide [1] (A) | | | Polyether Monohydric Alcohol (B) | | | | | | | Modified Polyalkylene Oxide Mixture | | | | |
|---|---|---|---|---|---|---|---|---|---|---|---|---|---|---|---|
| | | | | EO | PO | EO/PO | | | | | Proportion [%] | | | | |
| | Species | n | Molecular Weight | Molar Number (a) | Molar Number (b) | Molar Ratio a/b | R1 C Number | Molar Ratio B/A | Diisocyanate [2] (C) | NCO/OH | m = 1 | m = 2 | m = 3 | m = 4 | Mn |
| Comp. Example 3 | Poly-EO | 450 | 20000 | 20 | 0 | — | 18 | 0.55 | HMDI | 0.60 | 55 | 15 | 25 | 5 | 31,100 |
| Comp. Example 4 | Poly-EO | 90 | 4000 | 8 | 6 | 1.3 | 18 | 1.44 | HMDI | 1.00 | 50 | 35 | 10 | 5 | 9,500 |

[1] Poly-EO: Polyethylene Oxide
[2] HMDI: Dicyclohexylmethane-4,4'-diisocyanate, HDI: 1,6-Hexamethylene diisocyanate

TABLE 2

| | Viscosity of 2% by mass aqueous solution [Pa · s] (Water) | | | | | | | | Viscosity of 2% by mass aqueous solution [Pa · s] (1% Stearyl trimethyl ammonium chloride) | | | | | | | |
|---|---|---|---|---|---|---|---|---|---|---|---|---|---|---|---|---|
| | 0.001 [1/s] | 0.01 [1/s] | 0.1 [1/s] | 1 [1/s] | 10 [1/s] | 100 [1/s] | 1000 [1/s] | Transparency [%] | 0.001 [1/s] | 0.01 [1/s] | 0.1 [1/s] | 1 [1/s] | 10 [1/s] | 100 [1/s] | 1000 [1/s] | Transparency [%] |
| Example 1 | 400 | 430 | 410 | 160 | 21 | 2.5 | 0.67 | 91.5 | 400 | 430 | 410 | 400 | 21 | 2.5 | 0.67 | 91.5 |
| Example 2 | 650 | 600 | 600 | 250 | 45 | 15 | 1.2 | 88.7 | 650 | 600 | 600 | 250 | 45 | 15 | 1.2 | 88.7 |
| Example 3 | 350 | 350 | 330 | 110 | 15 | 1.5 | 0.35 | 87.5 | 350 | 350 | 330 | 110 | 15 | 1.5 | 0.35 | 87.5 |
| Comp. Example 1 | 700 | 650 | 630 | 200 | 58 | 25 | 3.5 | 56.5 | 700 | 650 | 630 | 200 | 58 | 25 | 3.5 | 56.5 |
| Comp. Example 2 | 350 | 350 | 330 | 120 | 15 | 1.5 | 0.07 | 85.5 | 350 | 350 | 330 | 120 | 15 | 1.5 | 0.07 | 62.5 |
| Comp. Example 3 | 2100 | 2200 | 2150 | 130 | 11 | 1.1 | 0.15 | 88.5 | 8.2 | 10.1 | 7.8 | 5.4 | 2.6 | 1.2 | 0.5 | 88.5 |
| Comp. Example 4 | 650 | 650 | 630 | 250 | 80 | 25 | 12 | 65.5 | 650 | 650 | 630 | 250 | 80 | 25 | 12 | 65.5 |

The invention claimed is:

1. A modified polyalkylene oxide obtained by reacting (A) a polyalkylene oxide compound, (B) a polyether monohydric alcohol, and (C) a diisocyanate compound;
   wherein the polyalkylene oxide compound (A) has a number average molecular weight of 6,000 to 30,000;
   wherein the polyether monohydric alcohol (B) comprises a random copolymer of ethylene oxide and propylene oxide, the random copolymer having a hydroxy group at one terminal and a linear-chain $C_{15-24}$ alkyl group at the other terminal, and having a ratio (a/b) of 1 to 2 wherein a represents the number of moles of ethylene oxide added and b represents the number of moles of propylene oxide added; and
   wherein the diisocyanate compound (C) is at least one member selected from the group consisting of compounds represented by formula (IV)

$$O=C=N-R^2-N=C=O \quad (IV)$$

wherein $R^2$ represents methyldiphenylene, hexamethylene, methyldicyclohexylene, 3-methyl-3,5,5-trimethylcyclohexylene, dimethylphenylene, or tolylene.

2. The modified polyalkylene oxide according to claim 1, wherein, with respect to the polyether monohydric alcohol (B), a is an integer of 5 to 10, and b is an integer of 5 to 8.

3. The modified polyalkylene oxide according to claim 1, wherein the polyether monohydric alcohol (B) has a number average molecular weight of 800 to 3,000.

4. The modified polyalkylene oxide according to claim 1, wherein the diisocyanate compound (C) is at least one member selected from the group consisting of dicyclohexylmethane-4,4'-diisocyanate, and 1,6-hexamethylene diisocyanate.

5. The modified polyalkylene oxide according to claim 1, wherein the reaction is carried out using 1 to 2 moles of the polyether monohydric alcohol (B) per mole of the polyalkylene oxide compound (A).

6. A cosmetic composition comprising the modified polyalkylene oxide according to claim 1.

7. The cosmetic composition according to claim 6, further comprising a cationic surfactant.

8. A molded article prepared by using the modified polyalkylene oxide according to claim 1.

9. The molded article according to claim 8, which is in the form of a sheet or a film.

* * * * *